(12) United States Patent
Okamoto (10) Patent No.: US 7,644,477 B2
(45) Date of Patent: Jan. 12, 2010

(54) CORPSE TREATMENT DEVICE

(75) Inventor: Toshiki Okamoto, Hiroshima (JP)

(73) Assignee: Risa Nishihara, Hiroshima (JP)

( * ) Notice: Subject to any disclaimer, the term of this patent is extended or adjusted under 35 U.S.C. 154(b) by 35 days.

(21) Appl. No.: 11/794,990

(22) PCT Filed: Jan. 18, 2005

(86) PCT No.: PCT/JP2005/000512

§ 371 (c)(1),
(2), (4) Date: Jul. 10, 2007

(87) PCT Pub. No.: WO2006/077617

PCT Pub. Date: Jul. 27, 2006

(65) Prior Publication Data

US 2008/0086856 A1    Apr. 17, 2008

(51) Int. Cl.
*A01N 1/00* (2006.01)
*A61F 13/15* (2006.01)
*A61F 13/20* (2006.01)
*B64D 10/00* (2006.01)

(52) U.S. Cl. .................. 27/21.1; 604/385.01; 604/15; 604/358; 604/367; 600/29

(58) Field of Classification Search .................. 27/21.1, 27/24.1; 604/15, 18, 385.17, 327, 328, 358, 604/367
See application file for complete search history.

(56) References Cited

U.S. PATENT DOCUMENTS 5,370,129 A    12/1994    Diaz et al.

(Continued)

FOREIGN PATENT DOCUMENTS

EP    0 105 669    4/1984

(Continued)

OTHER PUBLICATIONS

Translation of Fujishiyoku (JP 07-265367.*

(Continued)

*Primary Examiner*—Tatyana Zalukaeva
*Assistant Examiner*—Susan Su
(74) *Attorney, Agent, or Firm*—Studebaker & Brackett PC; Donald R. Studebaker (57) ABSTRACT

A closing member (16) is disengageably fitted to one end of a cylindrical-shaped guide member (4) to close an opening (4a) of the guide member (4). A water-absorbing agent (3) made of water-absorbing resin powder is accommodated in the guide member (4) toward the one end. A column-shaped plug member (2) made of water-swellable fibers is accommodated in the guide member (4) at a location closer to the other end than the water-absorbing agent (3). A push rod (5) is inserted into the guide member (4) through an opening (4b) thereof located at the other end. With the opening (4a) at the one end of the guide member (4) inserted in an anus, the push rod (5) is operated to push the water-absorbing agent (3) and the plug member (2) through the opening (4a) at the one end of the guide member (4) into a rectum. The plug member (2) absorbs water in internal contents and expands to plug the rectum, while the water-absorbing agent (3) also absorbs water in the internal contents. Thus, the internal contents can be prevented from leaking out through the anus.

5 Claims, 5 Drawing Sheets

U.S. PATENT DOCUMENTS

| | | | | |
|---|---|---|---|---|
| 5,676,660 | A * | 10/1997 | Mukaida et al. | 604/375 |
| 5,800,338 | A * | 9/1998 | Kollerup et al. | 600/29 |
| 6,368,341 | B1 | 4/2002 | Abrahamson | 606/213 |
| 6,595,974 | B1 * | 7/2003 | Pauley et al. | 604/385.18 |
| 6,958,057 | B2 * | 10/2005 | Berg et al. | 604/385.17 |
| 7,160,279 | B2 * | 1/2007 | Pauley et al. | 604/385.18 |
| 2003/0153864 | A1 * | 8/2003 | Chaffringeon | 604/15 |
| 2004/0254557 | A1 * | 12/2004 | Kraemer | 604/385.18 |
| 2005/0273044 | A1 * | 12/2005 | Gann et al. | 604/15 |
| 2006/0074391 | A1 * | 4/2006 | Hagberg et al. | 604/385.18 |

FOREIGN PATENT DOCUMENTS

| | | |
|---|---|---|
| JP | 49-40296 | 7/1972 |
| JP | 59-82854 | 5/1984 |
| JP | 2-136648 | 11/1990 |
| JP | 07-265367 | 10/1995 |
| JP | 3042138 | 7/1997 |
| JP | 3048402 | 2/1998 |
| JP | 10-298001 | 11/1998 |
| JP | 3056825 | 12/1998 |
| JP | 2001-161733 | 6/2001 |
| JP | 2002-085493 | 3/2002 |
| JP | 2002-248140 | 9/2002 |
| JP | 2002-275001 | 9/2002 |
| JP | 2002-315792 | 10/2002 |
| JP | 2003-111830 | 4/2003 |
| JP | 2005-329161 | 12/2005 |
| JP | 2006-187672 | 7/2006 |

OTHER PUBLICATIONS

Machine translation of Hirata (JP 3048402).*
International Search Report for PCT/JP2005/000512 Dated Feb. 22, 2005.
Notice of Reasons for Rejection mailed on Apr. 22, 2008 in the corresponding Japanese patent Application.

* cited by examiner

CORPSE TREATMENT DEVICE

TECHNICAL FIELD

This invention relates to corpse treatment devices used in treating dead human bodies and particularly relates to the technical field of prevention of leakage of internal contents in body cavities through orifices.

BACKGROUND ART

Generally, after a human dies, muscles of his or her body parts become flaccid so that, for example, rectum contents including residual feces and body fluids may leak through the anus or, if a female, internal contents may also leak from the vagina. If internal contents thus leak from body cavities, this is hygienically undesirable and affects the later operations such as body transport. Prevention of leakage of internal contents is conventionally implemented by plugging body cavities with a plug member, for example, as disclosed in Patent Document 1.

The plug member in Patent Document 1 is formed by sheathing with a water-soluble sheet a column made of water-swellable fibers that absorb water to swell and applying a lubricant to the sheet surface. In using the plug member, for example, for an anus, the treatment person puts one longitudinal end of the column on the anus and then pushes the other end thereof in the direction of insertion with his or her finger. Thus, the column is inserted, together with the sheet, in the rectum by the action of the lubricant. When the column is inserted in the rectum together with the sheet, the sheet dissolves in water in internal contents so that the water is absorbed into fibers of the column. The fibers having absorbed the water swell to expand the diameter of the column. The expanded column comes into tight contact with the inner wall of the rectum to plug the rectum, thereby preventing the leakage of internal contents through the anus.

Patent Document 1: Japanese Unexamined Patent Publication No. 2003-111830 (Page 3, Page 4, FIG. 1 and FIG. 2)

DISCLOSURE OF THE INVENTION

Problem to be Solved by the Invention

For example, when a human dies from a disease, a large volume of internal contents may be discharged owing to treatments during antecedent care, such as enema cleansing. In another case, even if he or she undergoes no antecedent treatment such as enema cleansing, the amount of water in internal contents may be larger owing to his or her personal specificity. When an antecedent treatment such as enema cleansing is undergone or when internal contents of the corpse contain a large amount of water, however, such a simple insertion of the plug member in the cavity as in Patent Document 1 may fail to fully absorb water in the internal contents. In such a case, the internal contents may flow between fibers in the column and then leak out of the cavity.

As for the plug member disclosed in Patent Document 1, the treatment person inserts the column made of fibers into the cavity by pushing in it with his or her finger. It can be considered that the column may lose its shape in the course of insertion to fail to be inserted in position and thereby degrade its effect of plugging the cavity. Therefore, the insertion of the column needs to be carried out carefully so as not to deform the column and is a troublesome work for the treatment person. Further, in order to surely insert the column into the body cavity, the treatment person needs to put his or her finger in the cavity. Therefore, the column insertion work is also a reluctant work in the treatment site.

The present invention has been made in view of the foregoing points and, therefore, its object is to prevent body internal contents from leaking out of body cavities even when an antecedent treatment such as enema cleansing is undergone or when the internal contents contain a large amount of water, and improve the operability of the treatment for preventing the leakage of the internal contents.

Means to Solve the Problems

To attain the above object, the corpse treatment device of the present invention accommodates a column and a water-absorbing agent in a cylindrical guide member and is configured to push the column and the water-absorbing agent into the body cavity using a push member.

Specifically, in a first aspect of the invention, a corpse treatment device comprises: a column that expands by absorbing water; a water-absorbing agent; a guide member that is formed in a cylindrical shape having openings at both ends, accommodates the column and the water-absorbing agent and is configured to guide the column and the water-absorbing agent into a body cavity; a closing member that is open at one end thereof and disengageably fitted to one end of the guide member; and a rod-shaped push member configured to be inserted into the guide member through the opening located at the other end and push out, through the opening of the guide member located at the one end, the column and the water-absorbing agent accommodated in the guide member, wherein the corpse treatment device is configured so that the column pushed through the opening of the guide member at the one end into the body cavity by the push member absorbs water in internal contents in the body cavity to expand until plugging the cavity and the water-absorbing agent absorbs water in the internal contents, thereby preventing the internal contents from leaking out of the cavity.

With this structure, since the opening at the one end of the guide member is closed by the closing member, this avoids the exit of the column and the water-absorbing agent, which are accommodated in the guide member, from the guide member through the opening at the one end prior to use. In inserting the column and the water-absorbing agent into a body cavity, the treatment person need only insert the one end of the guide member having the opening into the body cavity and then operate the push member. Thus, the closing member disengages from the opening at the one end of the guide member, the column is guided by the guide member so that it is inserted in the cavity to a predetermined location while keeping its desired shape, and the water-absorbing agent is likewise inserted. Therefore, the treatment person can easily and reliably insert the column and the water-absorbing agent into the body cavity without putting his or her finger in the cavity.

The column inserted into the body cavity absorbs water in internal contents to expand, thereby plugging the cavity. Even if the body has undergone enema cleansing or other antecedent treatment or contains a large amount of water in the internal contents, the water-absorbing agent also absorbs water in the internal contents, which prevents the internal contents from leaking out of the cavity.

In a second aspect of the invention, the water-absorbing agent in the first aspect of the invention is accommodated in the guide member at a location closer to the opening at the one end than the column.

With this structure, the water-absorbing agent is located deeper in the cavity than the column when it has been inserted in the body cavity. This allows the water-absorbing agent to absorb, deeper in the cavity, water in internal contents that might otherwise leak out from deeper in the cavity.

In a third aspect of the invention, the column in the first or second aspect of the invention is made of water-swellable fibers that swell by absorbing water.

With this structure, fibers forming the column absorb water in internal contents to swell so that the column expands until plugging the body cavity. In this condition, almost no clearance is left between each adjacent fibers forming the column.

In a fourth aspect of the invention, the column in the first or second aspect of the invention is made of a mixture of fibers and powder of water-absorbing resin that swells by absorbing water.

With this structure, powder of the water-absorbing resin absorbs water to swell so that the column expands until plugging the cavity. In this case, the swollen water-absorbing resin is retained between the fibers to form a lump as a whole.

In a fifth aspect of the invention, the water-absorbing agent in any one of the first to fourth aspects of the invention is made of powder of water-absorbing resin.

With this structure, the water-absorbing agent inserted in the body cavity is easy to diffuse in the cavity. This enables the water-absorbing agent to absorb water in internal contents within a wide area of the cavity.

In a sixth aspect of the invention, the powder of water-absorbing resin in the fifth aspect of the invention is gelled by absorbing water in the internal contents.

In this case, after absorbing water in internal contents, the water-absorbing agent is hard to flow.

EFFECTS OF THE INVENTION

In the first aspect of the invention, since the column and the water-absorbing agent, which are accommodated in the cylindrical guide member, can be inserted into the body cavity by the push member, this improves the operability of the treatment for preventing the leakage of internal contents from the body cavity. Further, since the column inserted in the body cavity expands until plugging the cavity and the water-absorbing agent also absorbs, independent of the column, water in internal contents, this prevents the internal contents from leaking out of the cavity even if the internal contents contain a large amount of water.

In the second aspect of the invention, since the water-absorbing agent is accommodated in the guide member at a location closer to the opening at the one end than the column, the water-absorbing agent can be placed deeper in the body cavity. Therefore, water in internal contents can be effectively absorbed deeper in the cavity by the water-absorbing agent.

In the third aspect of the invention, since the column is made of water-swellable fibers, almost no clearance is left between each adjacent fibers that have absorbed water in internal contents. This provides a sufficient effect of the column plugging the cavity.

In the fourth aspect of the invention, since the column is made of a mixture of powder of water-absorbing resin and fibers, the powder of the water-absorbing resin having absorbed water in internal contents forms a lump together with the fibers, which provides a sufficient effect of plugging the cavity.

In the fifth aspect of the invention, since the water-absorbing agent is made of powder of water-absorbing resin, the water-absorbing agent can absorb water in internal contents within a wide area of the cavity.

In the sixth aspect of the invention, since the water-absorbing agent is gelled to become hard to flow, this prevents the water-absorbing agent from leaking out of the cavity.

BRIEF DESCRIPTION OF THE DRAWINGS

FIG. 5 illustrates how to use the corpse treatment device.

EXPLANATION OF REFERENCE NUMERALS 1 corpse treatment device
2 plug member (column)
3 water-absorbing agent
4 guide member
4a one end opening
4b the other end opening
5 push rod (push member)
16 closing member

BEST MODE FOR CARRYING OUT THE INVENTION

An embodiment of the present invention will be described below in detail with reference to the drawings.

Figure 1:
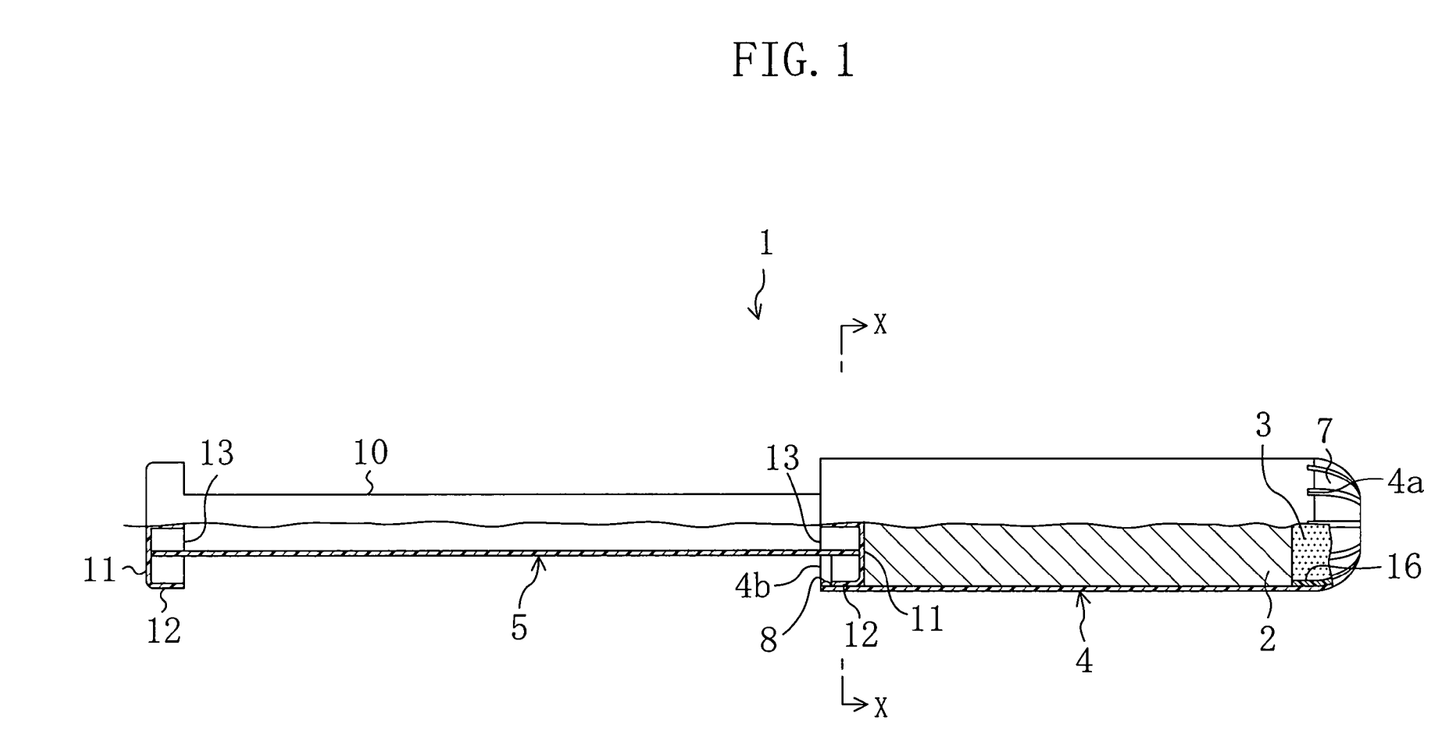
FIG. 1 is a partly cross-sectional view of a corpse treatment device according to an embodiment of the present invention.

FIG. 1 shows a corpse treatment device 1 according to an embodiment of the present invention. The treatment device 1 is for preventing internal contents in the rectum B of a body from leaking out through the anus A as shown in FIG. 5. The treatment device 1 includes a plug member 2 which is a column expandable by absorbing water, a water-absorbing agent 3, a cylindrical guide member 4 which accommodates and guides them into the rectum B of the body, and a push rod 5 serving as a push member for pushing the plug member 2 and the water-absorbing agent 3 out of the guide member 4.

The guide member 4 is obtained by forming a resin material into a cylindrical shape and has openings at both ends. The size of the guide member 4 is adapted to, for example, the shape of the rectum of a normal adult. Specifically, its axial dimension is selected between 85 mm and 100 mm both inclusive and its inner diameter is selected between 20 mm and 23 mm both inclusive. The thickness of the guide member 4 is selected at approximately 0.5 mm.

Figure 2:
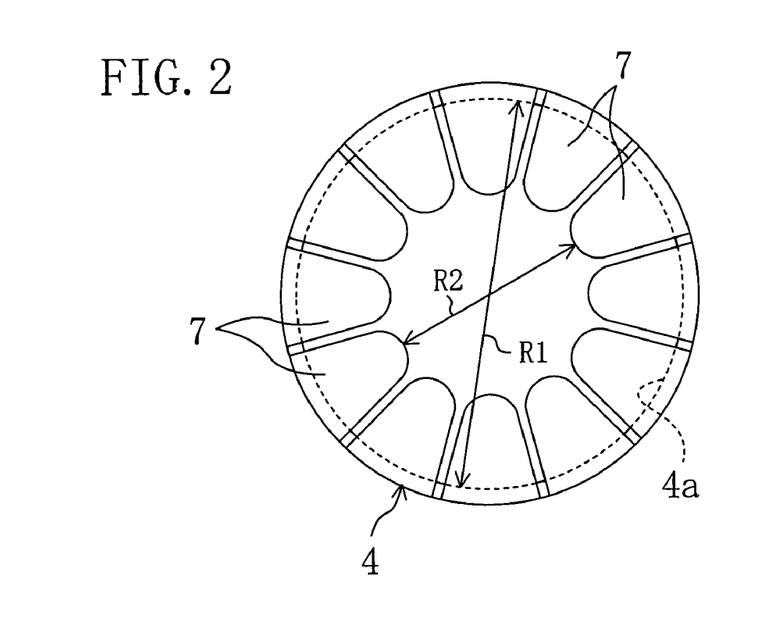
FIG. 2 is a front view of a guide member as viewed from its one end opening side.

As shown in FIG. 2, the edge of one end opening 4a at one end of the guide member 4 is provided integrally with a plurality of pinnae 7 extending toward the radial center of the one end opening 4a while curving. A clearance is created between each pair of pinnae 7 adjacent along the circumferential direction of the one end opening 4a. Each pinna 7 is flexibly formed so that the distal end part of the pinna 7 is displaced in the axial direction of the guide member 4. Further, the distance R2 between the distal ends of each radially opposed pair of pinnae 7 in the one end opening 4a is selected in the range of 0.3 to 0.7 times the inner diameter R1 of the guide member 4.

As shown in FIG. 1, the diameter of the other end opening 4b at the other end of the guide member 4 is selected to be substantially equal to the inner diameter R1 of the guide member 4. The inner surface of the guide member 4 is integrally formed, in the vicinity of the other end thereof, with a raised part 8 extending radially inward.

Figure 3:
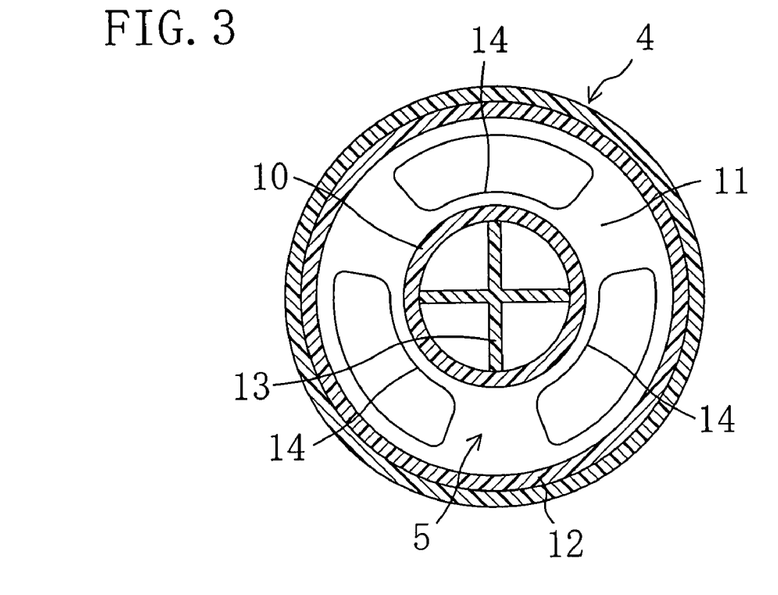
FIG. 3 is a cross-sectional view taken along the line X-X in FIG. 1.

The push rod 5 is composed of a rod member 10 and a pair of disc members 11 attached to both ends of the rod member 10. The pair of disc members 11 have a common shape and its outer diameter is selected to be substantially equal to the inner diameter R1 of the guide member 4. The peripheral edge of each disc member 11 is provided with a peripheral wall 12 that can slide on the inner surface of the guide member 4. The center of each disc member 11 is provided with a fitting part 13 of cross-shaped section extending toward the rod member 10. As shown in FIG. 3, each disc member 11 has three openings 14 formed, circumferentially spaced apart from each other, between the peripheral wall 12 and the fitting part 13. These openings 14 are for allowing air in the guide member 4 to flow through both sides of the disc member 11 in moving the push rod 5 in the axial direction of the guide member 4. The size and number of openings 14 can be flexibly selected.

The rod member 10 is formed into an elongated cylindrical shape and its length is selected to be longer than the axial dimension of the guide member 4. The fitting parts 13 of both the disc members 11 are fitted into both ends of the rod member 10 to join the rod member 10 and the disc members 11 together. Since the push rod 5 is formed by assembling the rod member 10 and the disc members 11 together in the above manner, the rod member 10 and the disc member 11 can be made of individual suitable materials.

The push rod 5 is inserted, with its one disc member 11, through the other end opening 4b into the guide member 4. With the push rod 5 inserted therein, a sliding resistance is created between the peripheral wall 12 of the disc member 11 and the inner surface of the guide member 4. Further, the push rod 5 is configured so that when it is inserted into the guide member 4, the peripheral wall 12 of the disc member 11 slides over and engages against the raised part 8 of the guide member 4 to hold the push rod 5 against sliding out of the guide member 4. Furthermore, since the disc members 11 at both ends of the push rod 5 have a common shape as described above, either disc member 11 has the same relation with the guide member 4 when inserted into it.

The plug member 2 is obtained by forming water-swellable fibers into a cylindrical shape. The outer diameter of the plug member 2 is selected to be substantially equal to the inner diameter R1 of the guide member 4 and the axial dimension thereof is selected to be shorter than that of the guide member 4. The size of the plug member 2 is changeable according to the body for which the treatment device 1 is used.

This embodiment employs, as the above-mentioned water-swellable fiber, LANSEAL®F or LANSEAL®K manufactured by Toyobo Co., Ltd., which is composed of an inner layer of an acrylic fiber and an outer layer of a water-absorbing resin. These water-swellable fibers have rates of water absorption that reach approximately 50% or more of the equilibrium absorption of water in approximately ten seconds after contacting water. These water-swellable fibers also have a property that once absorbing water, they do not release water even through the application of some degree of pressure and a property that they do not almost dissolve in water. Further, while the diameter of each water-swellable fiber after absorbing water expands up to approximately five or more times the diameter thereof before absorbing water, the length of each water-swellable fiber does not almost change between before and after absorbing water because it is kept by the acrylic fiber. Since the fiber material properties of each water-swellable fiber are taken on by the acrylic fiber, they are not almost degraded even if the water-absorbing resin forming the outer layer absorbs water.

The above water-swellable fibers have carboxyl groups. The carboxyl groups act to selectively adsorb ammonia in internal contents. This enables odor reduction.

The water-absorbing agent 3 is composed of powder of water-absorbing resin. The particle size of the powder ranges from 40 to 150 mesh, both inclusive. This embodiment employs, as the water-absorbing resin, acrylic cross-linked polymer. Acrylic cross-linked polymer has a property that it changes in gel form when absorbing water and becomes water-insoluble after gelled. Instead of acrylic cross-linked polymer, use can be made of other water-absorbing resins that do not release absorbed water, such as starch-acrylate graft copolymer, starch-acrylonitrile graft copolymer or cross-linked polyethylene oxide.

The water-absorbing agent 3 may be mixed with stabilized chlorine dioxide. The mixture of stabilized chlorine dioxide enables reduction of odor and germs. The water-absorbing agent 3 may be mixed with, instead of or besides stabilized chlorine dioxide, deodorant, germicide and/or antiseptic.

Figure 4:
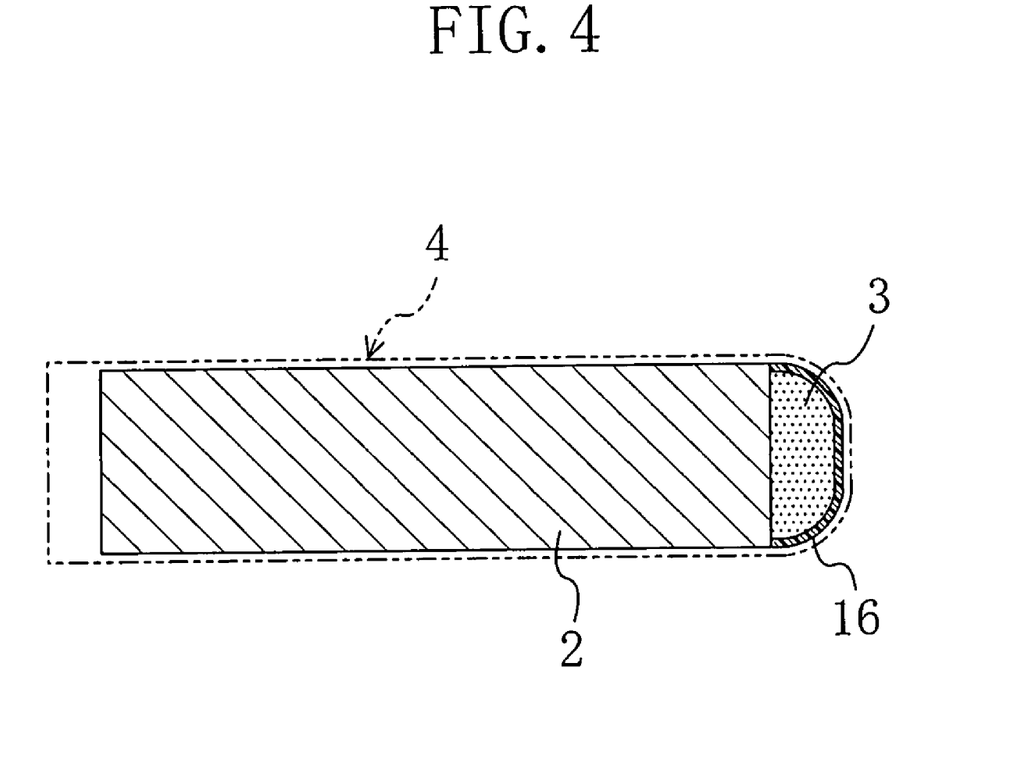
FIG. 4 is a cross-sectional view showing a closing member, a water-absorbing agent and a plug member.

As shown in FIGS. 1 and 4, the water-absorbing agent 3 is accommodated in a portion of the guide member 4 closer to the one end opening 4a than the plug member 2 and between a closing member 16 and the plug member 2. In this embodiment, the content of the water-absorbing agent 3 ranges from 0.10 to 3.00 g, both inclusive, and, for example, is set at 0.50 g. If the content of the water-absorbing agent 3 is selected in the range from 0.05 to 5.00 g, both inclusive, water in internal contents can be well absorbed.

The closing member 16 is obtained by forming biodegradable resin in the form of a hat that is open toward the other end of the guide member 4, and is also a component of the treatment device 1. The closing member 16 is accommodated in the guide member 4 in the vicinity of the one end opening 4a. The open-side part of the closing member 16 comes into tight contact with the inner surface of the guide member 4. The surface of the closing member 16 facing the pinnae 7 is formed to extend along the surfaces of the pinnae 7 located toward the inner space of the guide member 4. Thus, the closing member 16 is held against exit from the guide member 4 through the one end opening 4a by the pinnae 7.

When the plug member 2 is pushed toward the one end opening 4a by the push rod 5, the pinnae 7 are bent by the pushing force so that the closing member 16 gets out of the guide member 4 through the one end opening 4a and disengages from the guide member 4. The closing member 16 may be obtained by forming, for example, paper, cloth or absorbent cotton.

Next, a description will be made of how to assemble the corpse treatment device 1 having the above structure. First, the closing member 16 is inserted into the guide member 4 through the other end opening 4b. In doing so, the open side of the closing member 16 is faced toward the other end opening 4b. Since the closing member 16 is made of resin, it elastically deforms when sliding over the raised part 8, which reduces the force of insertion of the closing member 16 into the guide member 4.

Then, the water-absorbing agent 3 is put into the closing member 16, followed by the insertion of the plug member 2 into the guide member 4 through the other end opening 4b. The plug member 2 covers the open side of the closing member 16. Since the plug member 2 is made of fibers, it also elastically deforms when sliding over the raised part 8, which reduces the force of insertion of the plug member 2 into the guide member 4.

Thereafter, one of the disc members 11 of the push rod 5 is brought to bear on the end surface of the plug member 2 opposite to the closing member 16 and the plug member 2 is then pushed, together with the closing member 16, into the guide member 4 toward the one end opening 4a thereof by the push rod 5. This pushing operation is finished when the closing member 16 comes into abutment with the pinnae 7.

The closing member 16 and plug member 2 inserted into the guide member 4 are held against exit therefrom through the one end opening 4a by the pinnae 7 and held against exit therefrom through the other end opening 4b by the push rod 5. In this case, the distance R2 between the distal ends of each opposed pair of pinnae 7 is set at 0.7 times the inner diameter R1 of the guide member 4 or smaller. This enables the closing member 16 and plug member 2 to be surely prevented from exiting through the one end opening 4a, for example, when the treatment device 1 is transported.

Figure 5A:
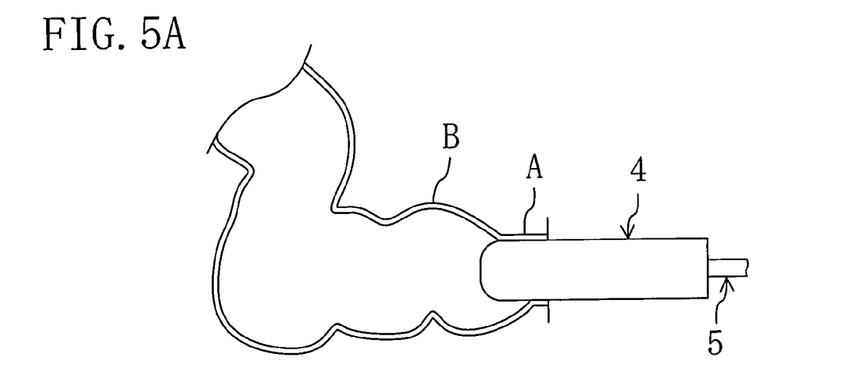
FIG. 5A is a view showing a condition in which the guide member is inserted in the rectum.

Next, a description will be made of how to use the corpse treatment device 1 configured as above with reference to FIG. 5. As shown in FIG. 5A, the lubricant is first applied to the outer surface of the guide member 4 and the guide member 4 is then inserted, beginning with the one end opening 4a side, several ten mm into the anus A. Thereafter, when the push rod 5 is pushed, its pushing force is transmitted to the plug member 2, the water-absorbing agent 3 and the closing member 16. The pushing force allows the closing member 16 to bend the pinnae 7 outward of the guide member 4, move from the guide member 4 through the one end opening 4a into the rectum B and disengage from the guide member 4. In this case, the distance R2 between the distal ends of each opposed pair of pinnae 7 is set at 0.3 or more times the inner diameter R1 of the guide member 4. Therefore, only a small pushing force is needed in pushing out the closing member 16, which facilitates the operation of the push rod 5.

Figure 5B:
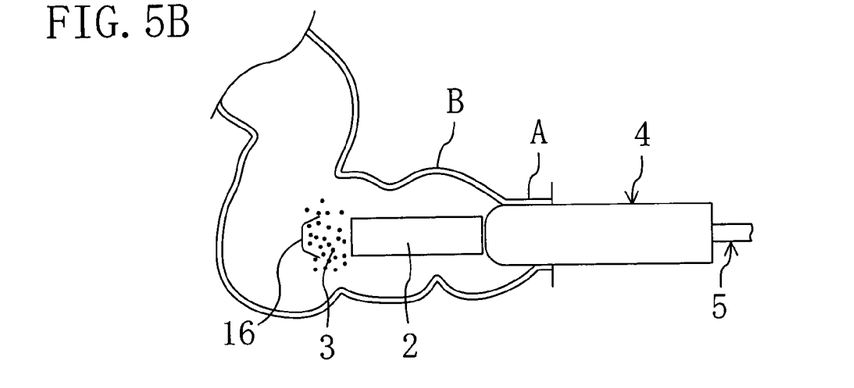
FIG. 5B is a view showing a condition in which the water-absorbing agent and the plug member are pushed from the guide member into the rectum.

Next to the closing member 16, the plug member 2 also moves into the rectum B as shown in FIG. 5B. At this time, the closing member 16 and the plug member 2 get away from each other so that the water-absorbing agent 3 disperses deeper in the rectum B than the plug member 2. In this manner, the plug member 2 is surely inserted in the rectum B to a predetermined location by the guide member 4 while keeping its desired shape and the water-absorbing agent 3 is likewise inserted thereinto by the guide member 4. Therefore, in inserting the plug member 2 and the water-absorbing agent 3 into the rectum B, there is no need for the treatment person to insert any finger into the anus A unlike the known art.

After the water-absorbing agent 3 and the plug member 2 have been inserted in the rectum B, the guide member 4 is pulled out of the anus A, resulting in completion of the treatment.

Thereafter, the water-swellable fibers of the plug member 2, which has been inserted in the rectum B, absorb water in internal contents in the rectum B to swell, so that the plug member 2 expands up to five or more times its diameter. When the plug member 2 thus expands, the outer peripheral surface of the plug member 2 comes into tight contact with the inner wall of the rectum B to plug the rectum B. Since, at this time, fibers forming the plug member 2 have swollen, they come into close contact with one another so that almost no clearance is left between each adjacent fibers. Further, since the water-swellable fibers do not change their fiber material properties after absorbing water, the plug member 2 becomes hard to get out of shape even after expanding.

Figure 5C:
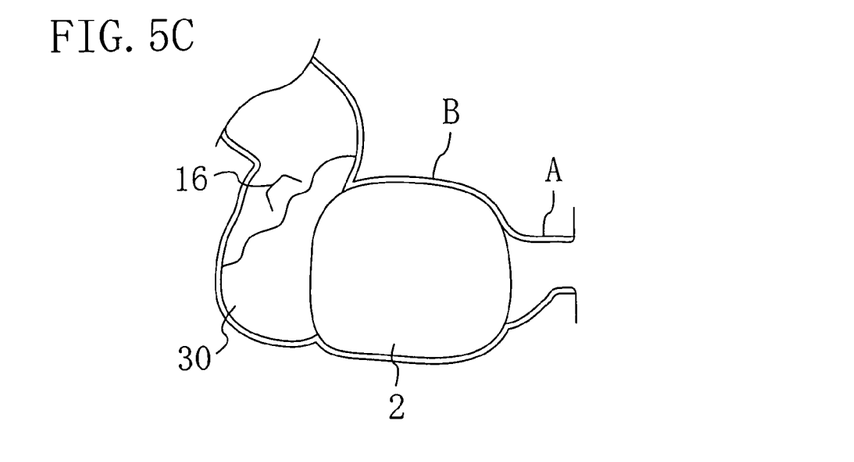
FIG. 5C is a view showing a condition in which the water-absorbing agent and the plug member have absorbed water in internal contents.

Referring to FIG. 5C, the water-absorbing agent 3 absorbs, deeper in the rectum B, water in internal contents to become gelled. The gelled water-absorbing agent is indicated at 30 in the figure. In this case, the content of water-absorbing agent 3 is at 0.10 g or more. Therefore, water in the internal contents can be absorbed with reliability by the water-absorbing agent 3. Since water in the internal contents is thus absorbed, this prevents the internal contents from leaking out through the anus A.

In the corpse treatment device 1 according to this embodiment, the water-absorbing agent 3 and the plug member 2 are inserted into the rectum B of a body through the anus A by the push rod 5. This improves the operability of the treatment for preventing the leakage of internal contents through the anus A. Further, since the water-absorbing agent 3 absorbs water in the internal contents in the rectum B, this prevents the internal contents from leaking out through the anus A even the body has undergone enema cleansing or other antecedent treatment or contains a large amount of water in the internal contents.

Furthermore, since the water-absorbing agent 3 is accommodated in the guide member 4 at a location closer to the one end opening 4a than the plug member 2, it can be inserted deeper in the rectum B. This allows the water-absorbing agent 3 to effectively absorb water in the internal contents deeper in the rectum B.

Furthermore, since the plug member 2 is made of water-swellable fibers, almost no clearance is left between each adjacent fibers that have absorbed water in the internal contents. This provides a sufficient effect of the plug member 2 plugging the rectum B.

Furthermore, since the water-absorbing agent 3 is made of water-absorbing resin powder, it is ease to diffuse in the rectum B. This enables the water-absorbing agent 3 to absorb water in the internal contents within a wide area of the rectum B.

Furthermore, since the water-absorbing agent 3 becomes gelled and hard to flow after absorbing water, this prevents the water-absorbing agent 3 from leaking out through the anus A.

Figure 6:
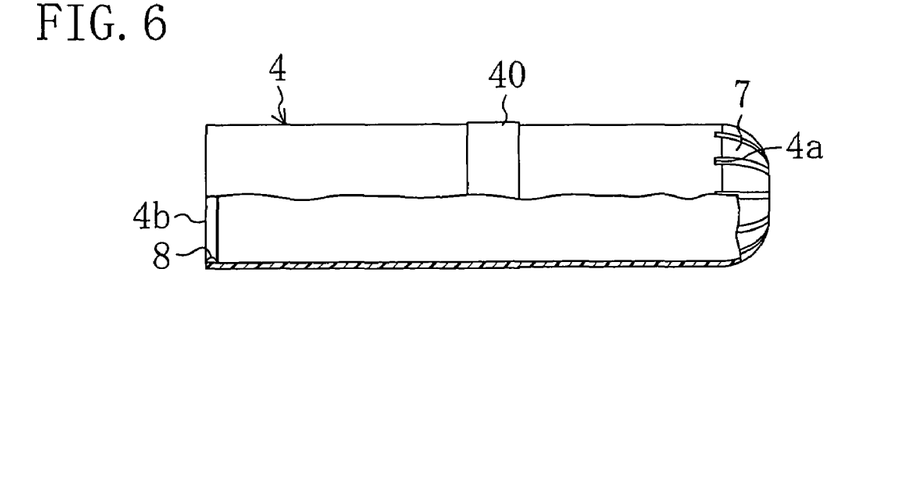
FIG. 6 is a partly cross-sectional view of a guide member according to Modification 1 of the above embodiment.

As in Modification 1 shown in FIG. 6, the guide member 4 may have a mark 40 which will give an indication of the degree of insertion thereof into the anus A. The mark 40 in this case is formed by giving the axial middle of the outer peripheral surface of the guide member 4 a different color from resin material forming the guide member 4. The position of the mark 40 can be flexibly selected. In inserting the guide member 4 into the anus A, the guide member 4 is inserted until the mark 40 reaches the vicinity of the anus A. This prevents shortage and excess of insertion of the guide member 4, thereby providing a secure placement of the water-absorbing agent 3 and the plug member 2 into predetermined locations of the rectum B. The mark 40 may be implemented by putting a seal, graining or embossing.

Figure 7:
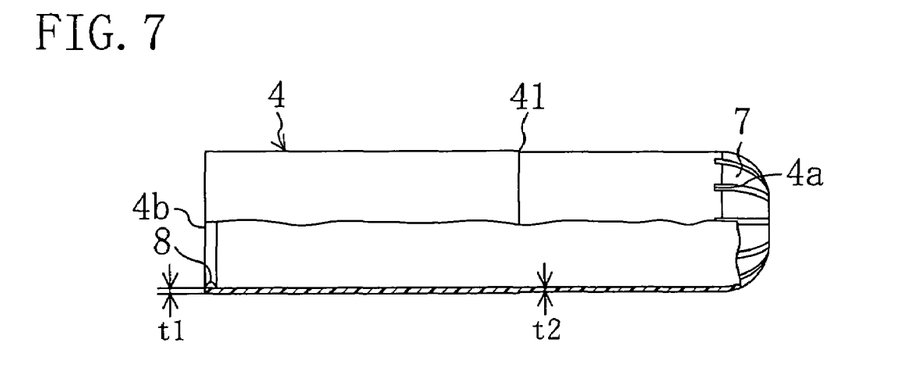
FIG. 7 is a corresponding view of FIG. 6, showing a guide member according to Modification 2 of the above embodiment.

In Modification 2 shown in FIG. 7, one side of the guide member 4 toward the one end has a smaller thickness t2 than the thickness t1 of the other side. Therefore, the one side thereof has a smaller outer diameter than the other side to form a shoulder 41. When the guide member 4 is being inserted into the anus A, the shoulder 41 reaches the anus A in good time. At this time, the force of insertion is increased.

This informs the treatment person of the degree of insertion of the guide member 4. That is, in Modification 2, the shoulder 41 gives an indication of the degree of insertion of the guide member 4.

Figure 8:
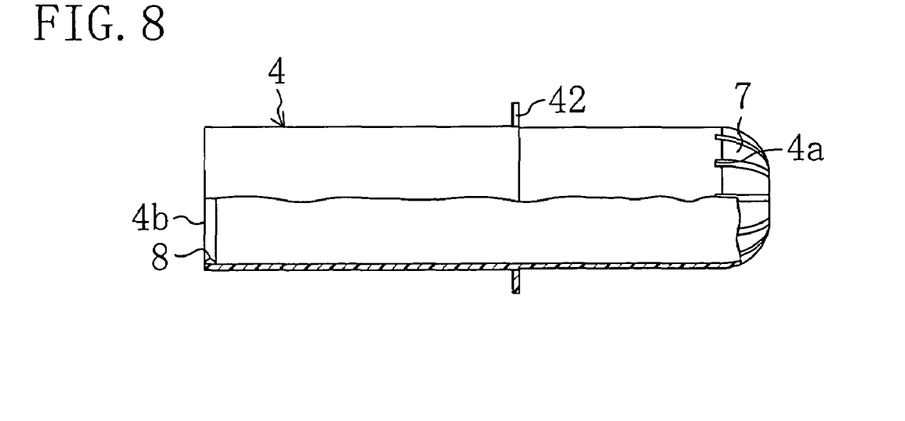
FIG. 8 is a corresponding view of FIG. 6, showing a guide member according to Modification 3 of the above embodiment.

In Modification 3 shown in FIG. 8, the outer peripheral surface of the guide member 4 is provided with a flange 42. When the guide member 4 is being inserted into the anus A, the flange 42 comes into abutment with the periphery of the anus A, so that the guide member 4 is inserted no more into the anus. That is, in Modification 3, the flange 42 gives an indication of the degree of insertion of the guide member 4.

This embodiment describes the case where the plug member 42 is made of water-swellable fibers only. The plug member 2 may be made of a mixture of another kind of fibers, such as cotton fibers, and the above-mentioned water-absorbing resin powder, though it is not shown. When the plug member made of such a mixture contacts water in internal contents, the water-absorbing resin swells so that the plug member expands until plugging the rectum B. During the time, the water-absorbing resin is gelled and retained between the fibers to form a lump as a whole. This provides a sufficient effect of the plug member 2 plugging the rectum B.

Further, this embodiment describes the case where the corpse treatment device 1 is used for the anus A. The corpse treatment device 1, however, can be used, for example, for the vagina. In this case, the guide member 4 and the plug member 2 have shapes adapting to the shape of the vagina. The shapes of the guide member 4 and the plug member 2 are changeable according to the body build or sex.

INDUSTRIAL APPLICABILITY

As described so far, the corpse treatment device according to the present invention can be used, for example, for preventing internal contents remaining in the rectum of a body from leaking out through the anus.

The invention claimed is:

1. A corpse treatment device comprising:
   a column;
   a water-absorbing agent made of a powder of water-absorbing resin;
   a guide member formed in a cylindrical shape having openings at both ends, said guide member accommodates the column and the water-absorbing agent and is configured to guide the column and the water-absorbing agent into a body cavity;
   a closing member disengageably fitted to and closing the opening at the distal end of the guide member; and
   a rod-shaped push member configured to be inserted into the guide member through the opening at the proximal end to push out the column and the water-absorbing agent accommodated in the guide member through the opening at the distal end of the guide member;
   wherein the closing member is configured to completely detach from the guide member when the column and water-absorbing agent are pushed through the opening at the distal end of the guide member into the body cavity by the push member;
   wherein the column is configured to expand until the cavity is plugged by absorbing water from internal contents in the body cavity and the water-absorbing agent is configured to absorb water from the internal contents, thereby preventing the internal contents from leaking out of the cavity; and
   wherein the water-absorbing agent is disposed adjacent to the column and in proximity of the opening at the distal end of the guide member.

2. The corpse treatment device of claim 1, wherein the water-absorbing agent is accommodated in the guide member at a location closer to the opening at the distal end of the guide member than the column.

3. The corpse treatment device of claim 1 or 2, wherein the column is made of water-swellable fibers that swell by absorbing water.

4. The corpse treatment device of claim 1, wherein the column is made of a mixture of fibers and a powder of water-absorbing resin that swells by absorbing water.

5. The corpse treatment device of claim 4, wherein the powder of water-absorbing resin is gelled by absorbing water in the internal contents.

* * * * *